United States Patent
Lee et al.

(10) Patent No.: US 10,481,118 B2
(45) Date of Patent: Nov. 19, 2019

(54) HYDROGEN SENSOR AND METHOD FOR MANUFACTURING THE SAME

(71) Applicant: SHIN SUNG C&T CO., LTD., Seoul (KR)

(72) Inventors: Woo Young Lee, Seoul (KR); Ji Sun Baek, Seoul (KR); Byung Jin Jang, Seoul (KR)

(73) Assignee: SHIN SUNG C&T CO., LTD., Seoul (KR)

( * ) Notice: Subject to any disclaimer, the term of this patent is extended or adjusted under 35 U.S.C. 154(b) by 0 days.

(21) Appl. No.: 15/402,550

(22) Filed: Jan. 10, 2017

(65) Prior Publication Data
US 2017/0241932 A1    Aug. 24, 2017

(30) Foreign Application Priority Data
Feb. 23, 2016    (KR) .................. 10-2016-0021533

(51) Int. Cl.
*G01N 27/12*    (2006.01)
*G01N 33/00*    (2006.01)

(52) U.S. Cl.
CPC ......... *G01N 27/125* (2013.01); *G01N 27/127* (2013.01); *G01N 27/129* (2013.01); *G01N 33/005* (2013.01)

(58) Field of Classification Search
CPC .. G01N 27/125; G01N 27/127; G01N 27/129; G01N 33/005
IPC ........................... G01N 27/125, 27/127, 27/129
See application file for complete search history.

(56) References Cited

FOREIGN PATENT DOCUMENTS

| KR | 20120088409 A | 8/2012 |
|----|---------------|--------|
| KR | 20150017422 A | 2/2015 |

OTHER PUBLICATIONS

Skucha, Karl, et al. "Palladium/silicon nanowire Schottky barrier-based hydrogen sensors." Sensors and Actuators B: Chemical145.1 (2010): 232-238.*

Q Peng, K., Z. O Huang, and Jing Zhu. "Fabrication of large-area silicon nanowire p—n junction diode arrays." Advanced Materials16.1 (2004): 73-76.*

Seo, Jungmok, et al. "Gas-driven ultrafast reversible switching of super-hydrophobic adhesion on palladium-coated silicon nanowires." Advanced Materials 25.30 (2013): 4139-4144.*

* cited by examiner

*Primary Examiner* — Robert J Eom
(74) *Attorney, Agent, or Firm* — Norton Rose Fulbright US LLP

(57) ABSTRACT

Disclosed are a hydrogen sensor which includes a P-type silicon nanowire array and a hydrogenation catalyst formed on a surface of the nanowire array, and a method of manufacturing the same.

10 Claims, 8 Drawing Sheets

HYDROGEN SENSOR AND METHOD FOR MANUFACTURING THE SAME

CROSS-REFERENCE TO RELATED APPLICATION

This application claims priority to and the benefit of Korean Patent Application No. 10-2016-0021533, filed on Feb. 23, 2016, the disclosure of which is incorporated herein by reference in its entirety.

BACKGROUND

1. Field of the Invention

The present invention relates to a hydrogen sensor and a method for manufacturing the same.

2. Discussion of Related Art

Recently, an environmental pollution problem such as global warming due to continuous use of fossil fuels and an energy supply and demand problem due to exhaustion of the fossil fuels have come to the fore. As a measure to overcome the problems, an interest in hydrogen which is a clean energy source and shows a development possibility in the future is increased, and development of hydrogen energy is proceeding rapidly. A variety of techniques for commodifying such hydrogen energy are currently at the stage of practical application. However, since hydrogen with a concentration of 4% or more has combustible and explosive properties when exposed in air, techniques for rapidly and accurately detecting a slight amount of hydrogen are vitally required to easily use the hydrogen energy, before hydrogen is used as clean energy.

Accordingly, studies on hydrogen sensor techniques for detecting hydrogen have recently proceeding continuously. This hydrogen sensor detects hydrogen using a change in an electric signal according to a reaction of hydrogen in a metallic material or a semiconductor material.

In this case, in order for the hydrogen sensor to rapidly and accurately detect hydrogen, it is very important to have high reactivity with respect to hydrogen. However, generally, hydrogen hardly reacts with the metallic material or the semiconductor material. To solve such a problem, techniques in which the reactivity to hydrogen is maximized by functionalizing palladium (Pd) as a catalyst for reaction with hydrogen in the metallic material or the semiconductor material have been proposed through many studies.

In Korean Patent No. 10-1191522, there is disclosed a hydrogen sensor using a silicon wafer and Pd. However, only the silicon water for manufacturing a silicon nanowire is described, and a study on silicon wafer properties has not proceeded.

SUMMARY OF THE INVENTION

The present invention is directed to providing a hydrogen sensor which includes a P-type silicon nanowire array and a hydrogenation catalyst formed on a surface of the nanowire array.

However, problems to be solved by the present disclosure are not limited to the above-described problems. Although not described here, other problems to be solved by the present invention can be clearly understood by those skilled in the art from the following description.

According to an aspect of the present invention, there is provided a hydrogen sensor including a P-type silicon nanowire array; and a hydrogenation catalyst formed on a surface of the nanowire array.

The nanowire array may be doped with a Group III element dopant.

A doping amount of the Group III element may be $10^{11}$ atoms/cm$^3$ to $10^{20}$ atom s/cm$^3$.

A specific resistance value of the nanowire array may be 0.001 Ωcm to 10,000 Ωcm.

The hydrogenation catalyst may include one or more metals selected from a group consisting of palladium (Pd), platinum (Pt), rhodium (Rd), aluminum (Al), nickel (Ni), manganese (Mn), molybdenum (Mo), magnesium (Mg) and vanadium (V).

The hydrogenation catalyst may be reduced into a metal hydride (MHx) after hydrogen exposure.

The hydrogen sensor may form a Schottky contact at an interface between the nanowire array and the hydrogenation catalyst after hydrogen exposure.

In the hydrogen sensor, sensitivity represented by the following Equation 1 may be 1% or more based on 1% hydrogen exposure:

$$\text{Sensitivity (\%)} = ((R_1 - R_0)/R_0) \times 100\% \qquad [\text{Equation 1}]$$

wherein $R_1$ is a maximum resistance value after hydrogen exposure, and $R_0$ is a resistance value before the hydrogen exposure.

According to another aspect of the present invention, there is provided a method for manufacturing a hydrogen sensor, including (a) forming a P-type silicon nanowire array by etching a P-type silicon wafer; and (b) depositing a hydrogenation catalyst on a surface of the nanowire array.

In the operation (a), the etching may be performed using a silver nitrate (AgNO$_3$) and hydrofluoric acid containing solution which includes 0.25 g to 1 g of silver nitrate, with respect to 100 ml of hydrofluoric acid.

In the operation (a), the etching may be performed at 50° C. to 70° C.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

The inventors have conducted a study on silicon wafer characteristics, have found that a hydrogen sensor using a silicon wafer and palladium (Pd) has very excellent sensitivity with respect to hydrogen exposure when using a P-type silicon wafer and thus have completed the invention.

Hereinafter, the present invention will be described in detail.

The preset invention provides a hydrogen sensor including a P-type silicon nanowire array and a hydrogenation catalyst formed on a surface of the nanowire array.

Most conventional thin film-type hydrogen sensors do not detect low-concentration hydrogen and have a reaction time of several minutes to several tens of minutes. To overcome these problems, the present invention is characterized by using a nanowire array of which a surface area is optimized.

Figure 1:
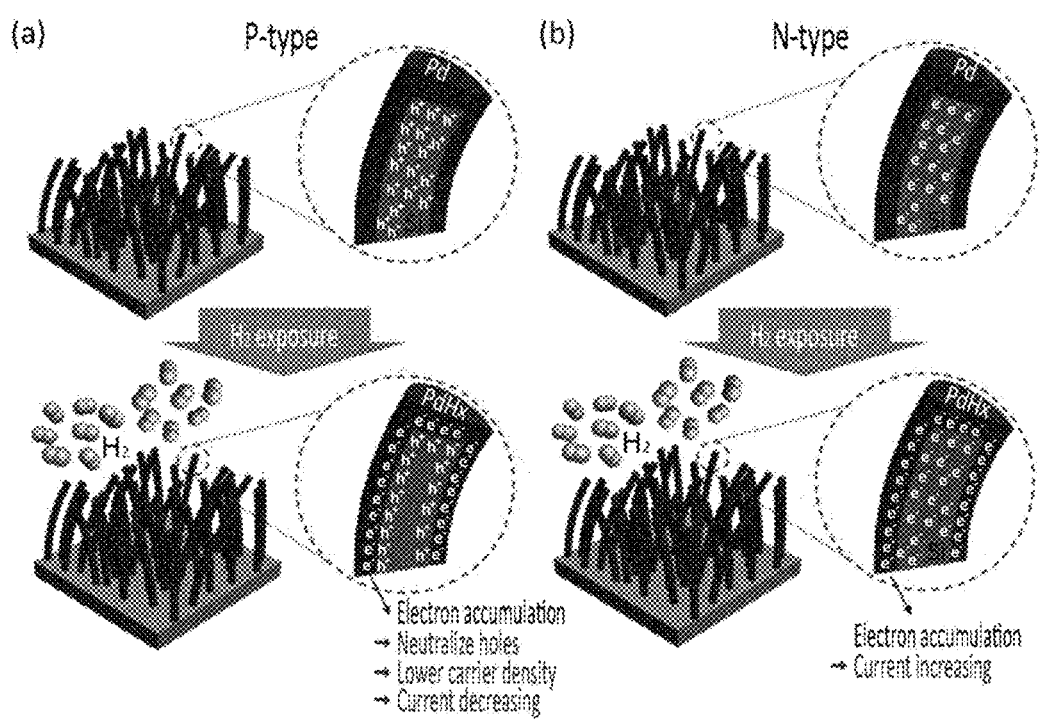
FIG. 1 is a graphical view comparing mechanisms (1) of a P-type silicon nanowire array-based hydrogen sensor and an N-type silicon nanowire array-based hydrogen sensor according to one embodiment of the present invention.

FIG. 1 is a graphical view comparing mechanisms (1) of a P-type silicon nanowire array-based hydrogen sensor and an N-type silicon nanowire array-based hydrogen sensor according to one embodiment of the present invention.

As illustrated in FIG. 1A, in a P-type silicon nanowire array-based hydrogen sensor according to one embodiment of the present invention, the hydrogenation catalyst is reduced into a metal hydride (MHx) after being exposed to hydrogen, and electrons (e⁻) may be concentrated at an interface between the nanowire array and the hydrogenation catalyst. Therefore, by forming the hydrogenation catalyst on a surface of a P-type silicon nanowire array having increased holes, the holes inside the nanowire array may be neutralized after hydrogen exposure and thus a current may be decreased.

On the other hand, as illustrated in FIG. 1B, in an N-type silicon nanowire array-based hydrogen sensor, similarly, the hydrogenation catalyst is reduced into the metal hydride (MHx) after being exposed to hydrogen, and electrons (e⁻) may be concentrated at the interface between the nanowire array and the hydrogenation catalyst. Therefore, by forming the hydrogenation catalyst on a surface of an N-type silicon nanowire array having an increased number of electrons, the current may be increased.

First, in the specification, the term "ohmic contact" is a phenomenon in which each of main carriers (holes or electrons) is smoothly moved, and in this case, the current is increased.

Also, in the specification, the term "Schottky contact" is a phenomenon in which movement of each of the main carriers (holes or electrons) is impossible due to formation of a Schottky barrier, and in this case, resistance is increased and the current is decreased.

Figure 2:
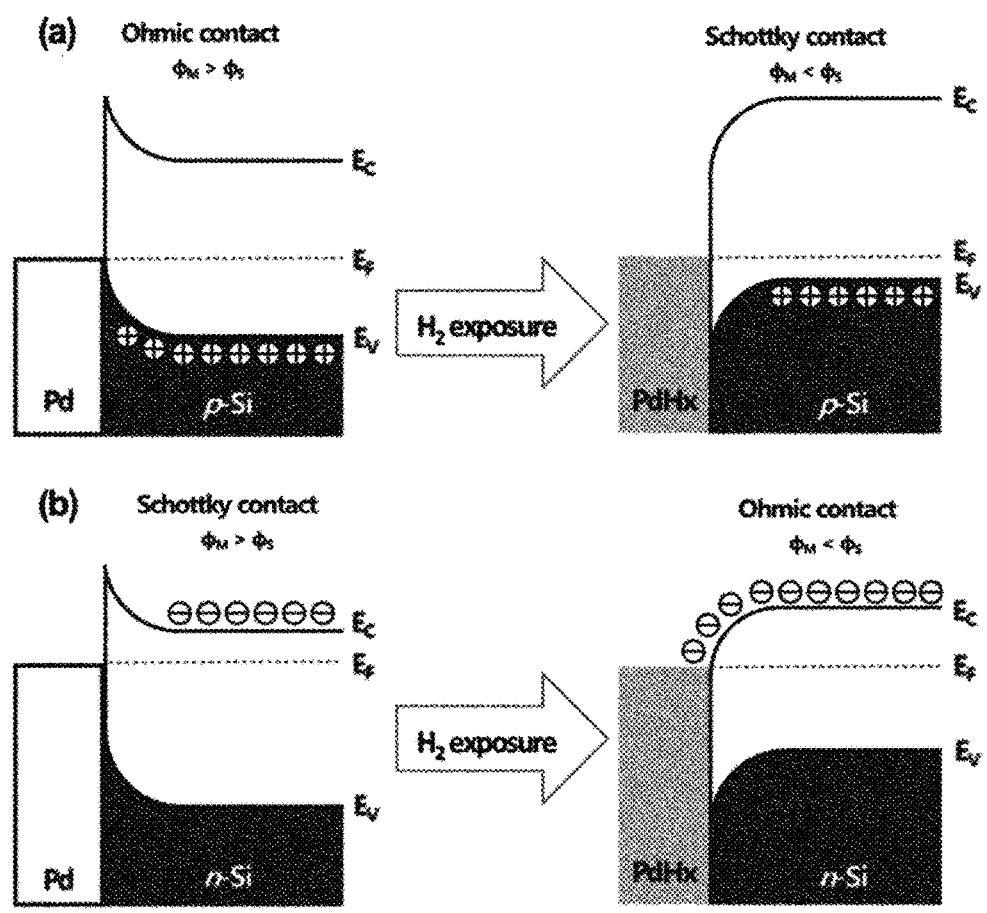
FIG. 2 is a graphical view comparing mechanisms (2) of the P-type silicon nanowire array-based hydrogen sensor and the N-type silicon nanowire array-based hydrogen sensor according to one embodiment of the present invention.

FIG. 2 is a graphical view comparing mechanisms (2) of the P-type silicon nanowire array-based hydrogen sensor and the N-type silicon nanowire array-based hydrogen sensor according to one embodiment of the present invention.

As illustrated in FIG. 2A, in the P-type silicon nanowire array-based hydrogen sensor according to one embodiment of the present invention, an ohmic contact may be formed at the interface between the nanowire array and the hydrogenation catalyst before exposure to hydrogen (a left side in the drawing). Specifically, a work function of Pd is 5.6 eV and that of P-type silicon is 4.9 eV. Since the work function of Pd is greater than that of P-type silicon, the ohmic contact is formed and the holes may be smoothly moved. Meanwhile, a Schottky contact may be formed at the interface between the nanowire array and the hydrogenation catalyst after the exposure to hydrogen (a right side in the drawing). Specifically, when being exposed to hydrogen, the work function of Pd is decreased according to a hydrogen exposure concentration, and thus the work function of PdHx becomes a negative number. By a difference between the work function of PdHx and the work function of P-type silicon, the Schottky barrier is formed and the current may be decreased.

That is, in the case of the P-type silicon nanowire array-based hydrogen sensor according to one embodiment of the present invention, when it is changed from the ohmic contact to the Schottky contact, the Schottky barrier becomes larger, as the difference between the work function of PdHx and the work function of P-type silicon is increased, and a decrease in a hole concentration occurs. Accordingly, a difference in the hole concentration (=n) inside the P-type silicon nanowire array occurs.

On the other hand, as illustrated in FIG. 2b, in the N-type silicon nanowire array-based hydrogen sensor, a Schottky contact may be formed at the interface between the nanowire array and the hydrogenation catalyst before the exposure to hydrogen (a left side in the drawing). Specifically, the work function of Pd is 5.6 eV and that of N-type silicon is 4.4 eV. Since the work function of Pd is greater than that of N-type silicon, the Schottky contact is formed and the electrons may not be moved due to formation of the Schottky barrier. Meanwhile, the ohmic contact may be formed at the interface between the nanowire array and the hydrogenation catalyst after the exposure to hydrogen (a right side in the drawing). Specifically, when being exposed to hydrogen, the work function of Pd is decreased according to the hydrogen exposure concentration, and thus the work function of PdHx becomes a negative number. Since the work function of PdHx is smaller than that of N-type silicon, the ohmic contact is formed and the electrons may be smoothly moved.

That is, in the case of the N-type silicon nanowire array-based hydrogen sensor, since a portion of the Schottky contact which is banded by a band structure is restored and changed into the ohmic contact, the number of electrons is increased by the banded portion. In the ohmic contact unlike the Schottky contact, there is not such a difference.

The hydrogen sensor according to the present invention includes the P-type silicon nanowire array.

First, the nanowire array is formed by etching a silicon wafer and characterized by a surface area thereof is optimized. The nanowire array may include any dopant which may form the holes therein, preferably includes a Group III element dopant, and more preferably includes one or more Group III element dopants selected from a group consisting of boron, gallium and indium, but is not limited thereto.

Specifically, a doping amount of the Group III element may be $10^{11}$ atoms/cm³ to $10^{20}$ atoms/cm³, but is not limited thereto. At this time, the doping amount of the Group III element determines a specific resistance value of the nanowire array.

The resistance value of the nanowire array may preferably be 0.001 Ωcm to 10,000 Ωcm, but is not limited thereto. At this time, the resistance value of the nanowire array is determined by the doping amount of the Group III element. When the resistance value of the nanowire array is less than 0.001 Ωcm, there is a problem that a change in the sensitivity is not great due to a large amount of the holes, and when the resistance value of the nanowire array is more than 10,000 Ωcm, there is a problem of difficulty in forming the nanowire array through etching of the silicon wafer.

Next, the hydrogen sensor according to the present invention includes the hydrogenation catalyst formed on the surface of the nanowire array.

The hydrogenation catalyst is formed on the surface of the nanowire array by a deposition process, may be entirely formed on the surface of the nanowire array and may form a core-shell structure, or may be partially formed on the surface of the nanowire array. At this time, the hydrogenation catalyst may be formed in the form of a film or a particle.

The hydrogenation catalyst may include one or more metals selected from a group consisting of palladium (Pd), platinum (Pt), rhodium (Rd), aluminum (Al), nickel (Ni), manganese (Mn), molybdenum (Mo), magnesium (Mg) and vanadium (V), and preferably includes Pd but is not limited thereto.

Since the hydrogenation catalyst may be reduced into the metal hydride (MHx) after the hydrogen exposure, electrons (e⁻) are concentrated at the interface between the nanowire array and the hydrogenation catalyst, and the holes inside the nanowire array are neutralized, and thus current may be decreased. Alternatively, the current may be decreased by forming the Schottky contact at the interface between the nanowire array and the hydrogenation catalyst.

Specifically, the metal hydride (MHx) may include a state in which one or more metals selected from a group consisting of palladium (Pd), platinum (Pt), rhodium (Rd), aluminum (Al), nickel (Ni), manganese (Mn), molybdenum (Mo), magnesium (Mg) and vanadium (V) is reduced, and preferably includes a state in which Pd is reduced but is not limited thereto.

The hydrogenation catalyst may have a thickness of 1 nm to 20 nm but is not limited thereto. At this time, the hydrogenation catalyst may be formed by the deposition process such as a sputtering method. When the thickness of the hydrogenation catalyst is less than 1 nm, there is a problem that a reaction with respect to hydrogen is not performed, and when the thickness of the hydrogenation catalyst is more than 20 nm, there is a problem that a recovery time is increased when being exposed to the air for reaction recovery after the hydrogen exposure.

In the hydrogen sensor, the Schottky contact may be formed at the interface between the nanowire array and the hydrogenation catalyst after the hydrogen exposure. Due to the Schottky contact, unlike the ohmic contact, it is possible to detect hydrogen according to hydrogen exposure concentration.

In the hydrogen sensor, the sensitivity represented by the following Equation 1 may preferably be 100% or more based on 1% hydrogen exposure, and more preferably be 1000% or more, but is not limited thereto.

Sensitivity (%)=(($R_1$−$R_0$)/$R_0$)×100%    [Equation 1]

$R_1$ is a maximum surface resistance value after 1% hydrogen exposure, and $R_0$ is a surface resistance value before 1% hydrogen exposure.

That is, the present invention relates to the hydrogen sensor which includes the P-type silicon nanowire array and the hydrogenation catalyst formed on the surface of the nanowire array, and a method for manufacturing the same.

The hydrogenation catalyst is reduced into the metal hydride (MEN) after the hydrogen exposure, and electrons (e⁻) are concentrated at the interface between the nanowire array and the hydrogenation catalyst, and the holes inside the nanowire array are neutralized, and thus current may be reduced. Alternatively, the current may be reduced by forming the Schottky contact at the interface between the nanowire array and the hydrogenation catalyst.

Accordingly, the hydrogen sensor according to the present invention has a rapid reaction time with respect to hydrogen exposure in oil, water and air and very excellent sensitivity, may be applied to various power facilities such as a transformer in which there is a concern about that hydrogen is generated due to deterioration, and may also be used in human breath analysis.

Method for Manufacturing Hydrogen Sensor

The present invention provides a method of manufacturing a hydrogen sensor, including (a) forming a P-type silicon nanowire array by etching a P-type silicon wafer; and (b) depositing a hydrogenation catalyst on a surface of the nanowire array.

First, the method of manufacturing the hydrogen sensor according to the present invention includes an operation (a) of forming the P-type silicon nanowire array by etching the P-type silicon wafer.

Specifically, the etching process is performed by repeating an operation of reducing silver ions, oxidizing silicon and reducing fluorine ions. Specific reaction equations 1 to 3 are as follows.

$$Ag^+ + e^- \rightarrow Ag(s) \quad (1)$$

$$Si(s) + 2H_2O \rightarrow SiO_2 + 4H^+ + 4e^- \quad (2)$$

$$SiO_2(s) + 6HF \rightarrow H_2SiF_6 + 2H_2O \quad (3)$$

The etching method uses a silver nitrate ($AgNO_3$) and hydrofluoric acid containing solution. The solution may preferably include 0.25 g to 1 g of silver nitrate, and more preferably, 0.5 g to 1 g with respect to 100 ml of hydrofluoric acid, but is not limited thereto.

Figure 3:
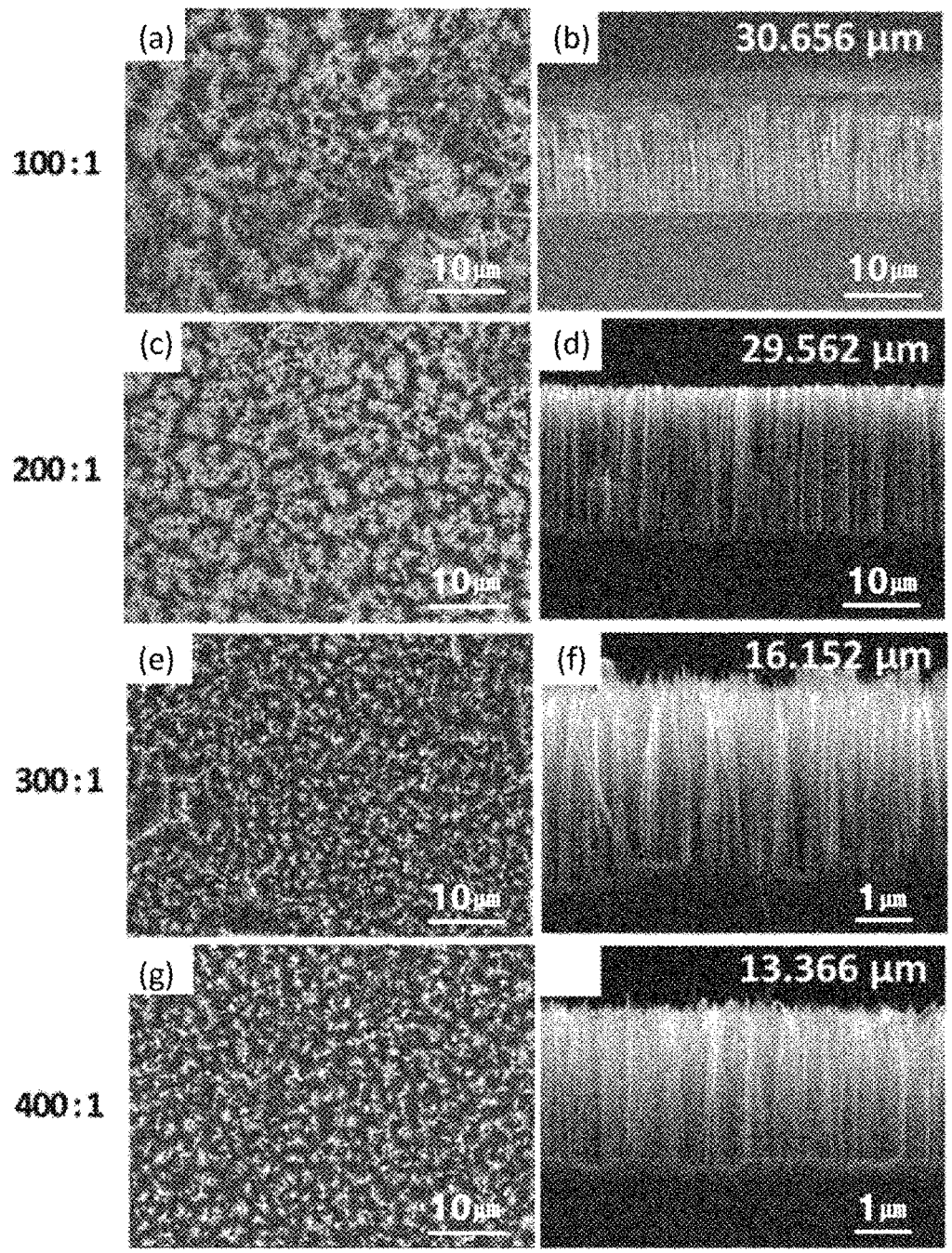
FIG. 3 is a SEM photograph comparing a surface area of a P-type silicon nanowire array according to one embodiment of the present invention based on concentrations of a silver nitrate (AgNO$_3$)- and hydrofluoric acid-containing solution.

FIG. 3 is a SEM photograph comparing a surface area of the P-type silicon nanowire array according to one embodiment of the present invention based on concentrations of the silver nitrate ($AgNO_3$)- and hydrofluoric acid-containing solution.

At this time, 100:1 refers to 100 ml of hydrofluoric acid: 1 g of silver nitrate, 200:1 refers to 100 ml of hydrofluoric acid: 0.5 g of silver nitrate, 300:1 refers to 100 ml of hydrofluoric acid: ⅓ g of silver nitrate, and 400:1 refers to 100 ml of hydrofluoric acid: 0.25 g of silver nitrate.

As illustrated in FIG. 3, when 0.5 g of silver nitrate is included with respect to 100 ml of hydrofluoric acid (200:1), it was confirmed that a specific surface area of the P-type silicon nanowire array is maximized and it is advantageous in a hydrogen adsorption reaction.

Also, the etching method may preferably be performed at 50° C. to 70° C. but is not limited thereto. At this time, when the etching process is performed at less than 50° C., there is a problem that an activated reaction of the etching solution is not smoothly performed, and when the etching process is performed at more than 70° C., there is a problem that the nanowire array may not be formed vertically due to over-etching. That is, the present invention is characterized in that the etching of the silicon wafer is not performed at room temperature corresponding to a typical etching temperature but is performed at a high temperature.

Next, the method of manufacturing the hydrogen sensor according to the present invention includes an operation (b) of depositing the hydrogenation catalyst on the surface of the nanowire array.

By the deposition process, the hydrogenation catalyst may be formed on the surface of the nanowire array in the form of a film or a particle.

The deposition method may be one or more well-known methods selected from a group consisting of a sputtering method, a vacuum deposition method, a chemical vapor deposition method, an atomic layer deposition method, an ion beam deposition method, a screen printing method, a spray dip coating method, a tape casting method and an inkjet method, and preferably may be the sputtering method but is not limited thereto.

Hereafter, exemplary embodiments will be provided to help understanding of the present invention. However, the following embodiments are merely provided for easier understanding of the invention, and thus the present invention is not intended to be limited thereto.

Embodiment

Embodiment

A 10% HF solution was manufactured by mixing a 50% HF solution and deionized water at a volume ratio of 1:4. An etching solution was manufactured by mixing the 10% HF solution with 0.5 g of silver nitrate. At this time, a temperature of a hot plate was maintained at about 60° C., and the etching solution was heated for about 1 hour.

Meanwhile, a P-type silicon wafer was prepared by doping a silicon wafer with $10^{15}$ atoms/cm$^3$ to $10^{16}$ atoms/cm$^3$ of boron. At this time, the specific resistance value of the P-type silicon wafer is 1 Ωcm to 10 Ωcm, and the P-type silicon wafer is in a single side polished state without an oxidized layer.

Then, the P-type silicon wafer was washed every 20 minutes with a sequence of acetone, methanol and deionized water in an ultrasonic treatment method. The washed P-type silicon wafer was soaked for about 10 seconds in a 50% HF solution, and a natural oxidized layer was removed.

The P-type silicon wafer from which the natural oxidized layer was removed was soaked in the etching solution, taken out after about 1 hour, rinsed with deionized water and then soaked again in a nitric acid solution, and thus residual Ag particles were removed.

The P-type silicon wafer from which the Ag particles were removed was rinsed with deionized water and then dried by a hot plate. Accordingly, the P-type silicon nanowire array was manufactured.

A hydrogen sensor was manufactured by depositing Pd on the surface of the P-type silicon nanowire array using a sputtering apparatus. At this time, a thickness of Pd was about 10 nm.

Figure 4:
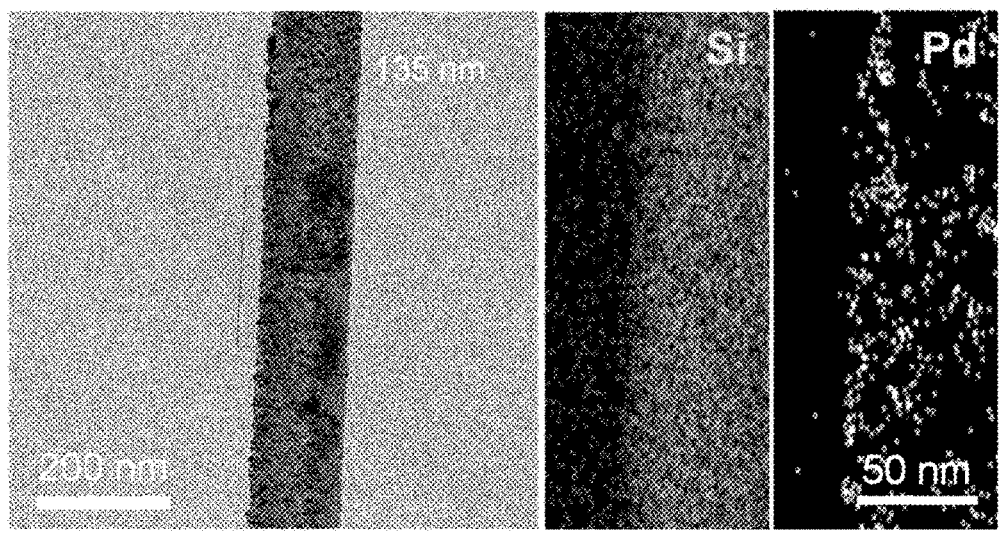
FIG. 4 is a TEM photograph illustrating a surface of a silicon nanowire according to one embodiment of the present invention.

FIG. 4 is a TEM photograph illustrating a surface of a silicon nanowire according to one embodiment of the present invention.

Meanwhile, as a result of observing a surface of the P-type silicon nanowire manufactured as described above with a transmission electron microscope (TEM), it was confirmed that a black dot type substance is deposited on the surface of the silicon nanowire, as illustrated in the TEM photograph of FIG. 4. Also, it was also confirmed through an energy dispersive X-ray spectroscopy (EDS) analysis that the block dot type substance is Pd.

Comparative Example

A 10% HF solution was manufactured by mixing a 50% HF solution and deionized water at a volume ratio of 1:4. An etching solution was manufactured by mixing the 10% HF solution with 0.5 g of silver nitrate. At this time, while a temperature of a hot plate was maintained at about 60° C., the etching solution was heated for about 1 hour.

Meanwhile, an N-type silicon wafer was prepared by doping a silicon wafer with $10^{14}$ atoms/cm$^3$ to $10^{15}$ atoms/cm$^3$ of phosphate. At this time, the specific resistance value of the N-type silicon wafer is 10 Ωcm to 10 Ωcm, and the N-type silicon wafer is in a single side polished state without an oxidized layer.

Then, the N-type silicon wafer was washed every 20 minutes with a sequence of acetone, methanol and deionized water in an ultrasonic treatment method. The washed N-type silicon wafer was soaked for about 10 seconds in the HF solution of 50%, and a natural oxidized layer was removed.

The N-type silicon wafer from which the natural oxidized layer was removed was soaked in the etching solution, taken out after about 1 hour, rinsed with deionized water and then soaked again in a nitric acid solution, and thus residual Ag particles were removed.

The N-type silicon wafer from which the Ag particles were removed was rinsed with deionized water and then dried by a hot plate. Accordingly, the N-type silicon nanowire array was manufactured.

A hydrogen sensor was manufactured by depositing Pd on the surface of the N-type silicon nanowire array using a sputtering apparatus. At this time, a thickness of Pd was about 30 nm.

Figure 5:
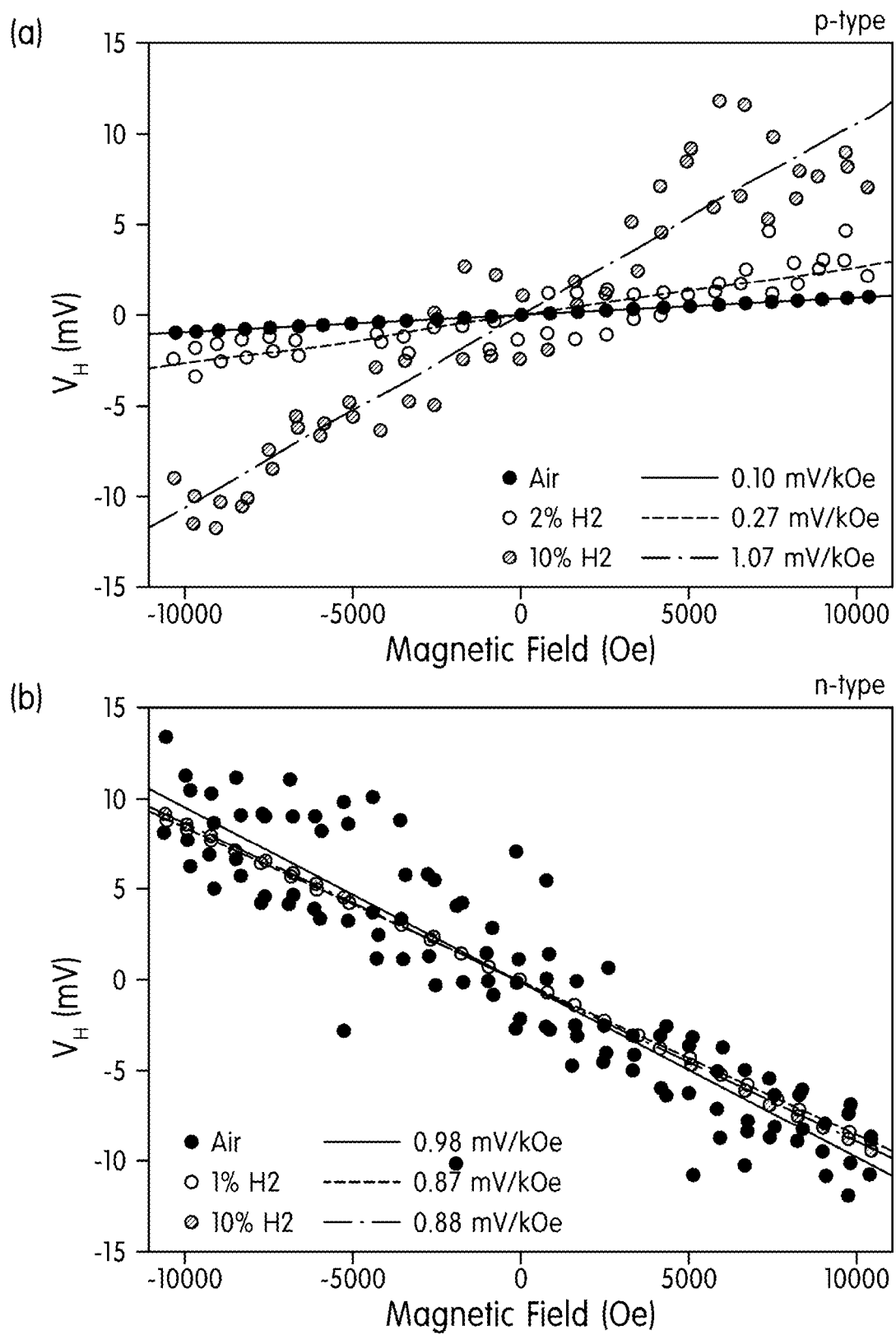
FIG. 5 is a graph illustrating a voltage ($V_H$) with respect to a magnetic field of the hydrogen sensor according to a comparative example and an embodiment of the present invention based on each hydrogen exposure concentration.

FIG. 5 is a graph illustrating a voltage ($V_H$) with respect to a magnetic field of the hydrogen sensor according to the comparative example and the embodiment of the present invention based on each hydrogen exposure concentration.

As illustrated in FIG. 5A, in a hole measurement result, it is confirmed that a voltage $V_H$ (=$V_H$/B) with respect to a magnetic field of the P-type silicon nanowire array-based hydrogen sensor according to the embodiment is increased as a hydrogen exposure concentration is increased. At this time, it can be understood from the equation of $V_H$=-IB/nte that the voltage $V_H$ (=$V_H$/B) with respect to the magnetic field is in reverse proportion to a hole concentration (=n) inside the P-type silicon nanowire array (referring to Table 1).

TABLE 1

| Hydrogen exposure concentration(%) | $V_H$/B (mV/kOe) | Hole concentration |
|---|---|---|
| 0 | 0.10 | 6.25E+19 |
| 2 | 0.27 | 2.31E+19 |
| 10 | 1.07 | 5.84E+18 |

That is, it is confirmed that the hole concentration (=n) inside the P-type silicon nanowire array is decreased as the hydrogen exposure concentration is increased. This is because the hydrogenation catalyst is reduced into a metal hydride after the hydrogen exposure and electrons (e⁻) are concentrated at the interface between the nanowire array and the hydrogenation catalyst and thus the holes inside the nanowire array are neutralized. Another reason is because the Schottky contact is formed at the interface between the nanowire array and the hydrogenation catalyst.

As illustrated in FIG. 5B, in the hole measurement result, it is confirmed that the voltage $V_H$ (=$V_H$/B) with respect to a magnetic field of the N-type silicon nanowire array-based hydrogen sensor according to the embodiment is decreased when exposed to hydrogen. At this time, it can be understood from the equation of $V_H$=−IB/nte that the voltage $V_H$ (=$V_H$/B) with respect to the magnetic field is in reverse proportion to an electron concentration (=n) inside the N-type silicon nanowire array (referring to Table 2).

TABLE 2

| Hydrogen exposure concentration(%) | $V_H$/B (mV/kOe) | Electron concentration |
|---|---|---|
| 0 | 0.98 | 6.38E+18 |
| 1 | 0.87 | 7.18E+18 |
| 10 | 0.88 | 7.10E+18 |

That is, it is confirmed that the electron concentration (=n) inside the N-type silicon nanowire array is increased when exposed to hydrogen. This is because the hydrogenation catalyst is reduced into a metal hydride after the hydrogen exposure and electrons (e−) are concentrated at the interface between the nanowire array and the hydrogenation catalyst and thus the number of electrons inside the nanowire array is increased. Another reason is because the ohmic contact is formed at the interface between the nanowire array and the hydrogenation catalyst.

Figure 6:
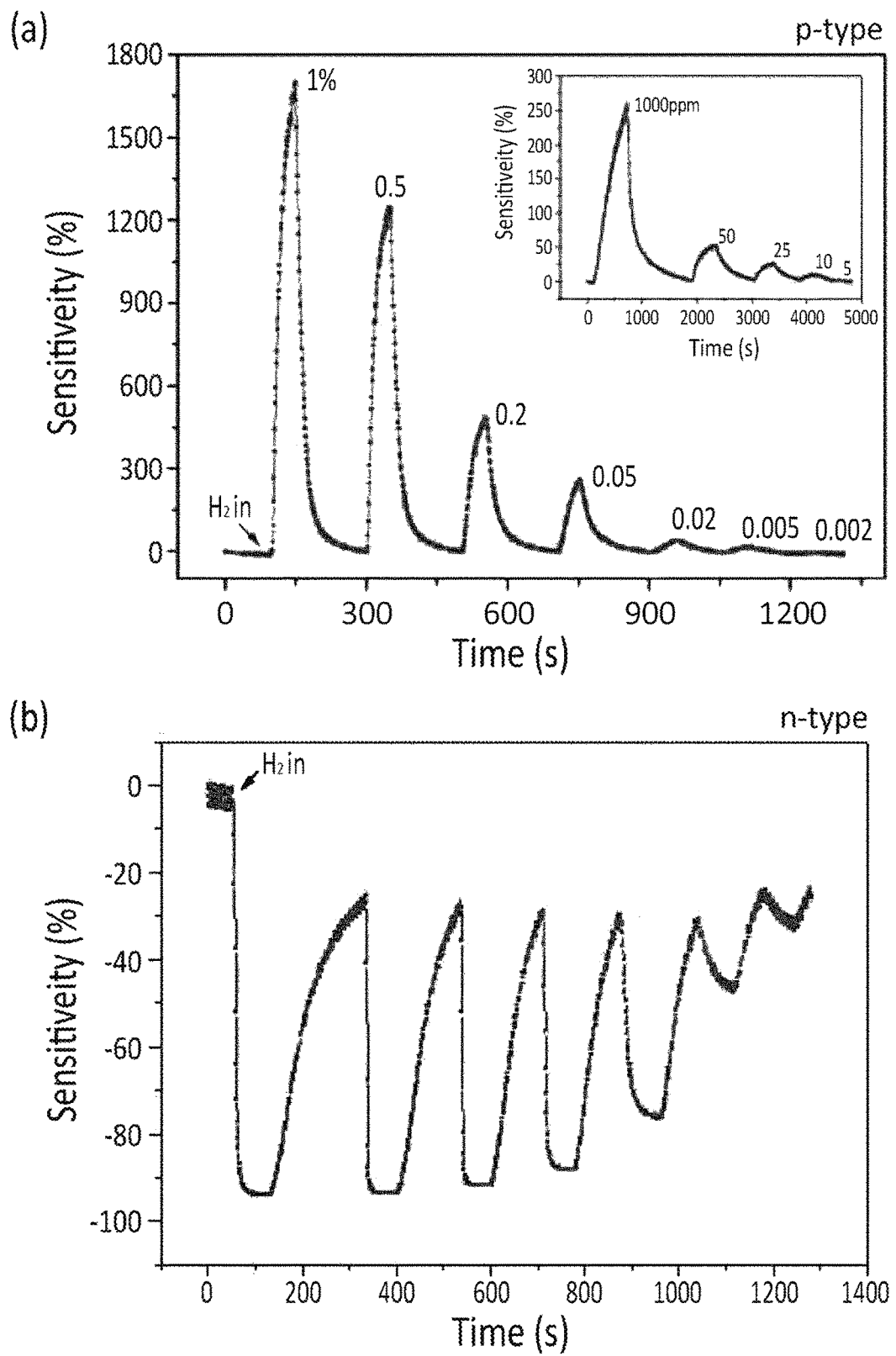
FIG. 6 is a graph comparing sensitivity and a reaction time of the hydrogen sensor according to a comparative example and an embodiment of the present invention with respect to hydrogen exposure in air.

FIG. 6 is a graph comparing the sensitivity and the reaction time of the hydrogen sensor according to the comparative example and the embodiment of the present invention with respect to the hydrogen exposure in air (1% hydrogen).

As illustrated in FIG. 6, as a result of monitoring a change in electrical resistance in real time, it is confirmed that the sensitivity of the hydrogen sensor with respect to hydrogen exposure in the air (1% hydrogen) according to the embodiment of the present invention is 1734% and the reaction time ($I_{90}$) thereof is 8 seconds or less. However, it is confirmed that the sensitivity of the hydrogen sensor with respect to the hydrogen exposure in the air (1% hydrogen) according to the comparative example is −94% and the reaction time ($I_{90}$) thereof is 38 seconds or less.

That is, in the case of the hydrogen sensor according to the comparative example, the reaction time is relatively fast by using the nanowire array having a larger surface area. However, as compared with the hydrogen sensor according to the embodiment, the sensitivity with respect to hydrogen exposure is considerably lowered, and the reaction time is also relatively longer.

Figure 7:
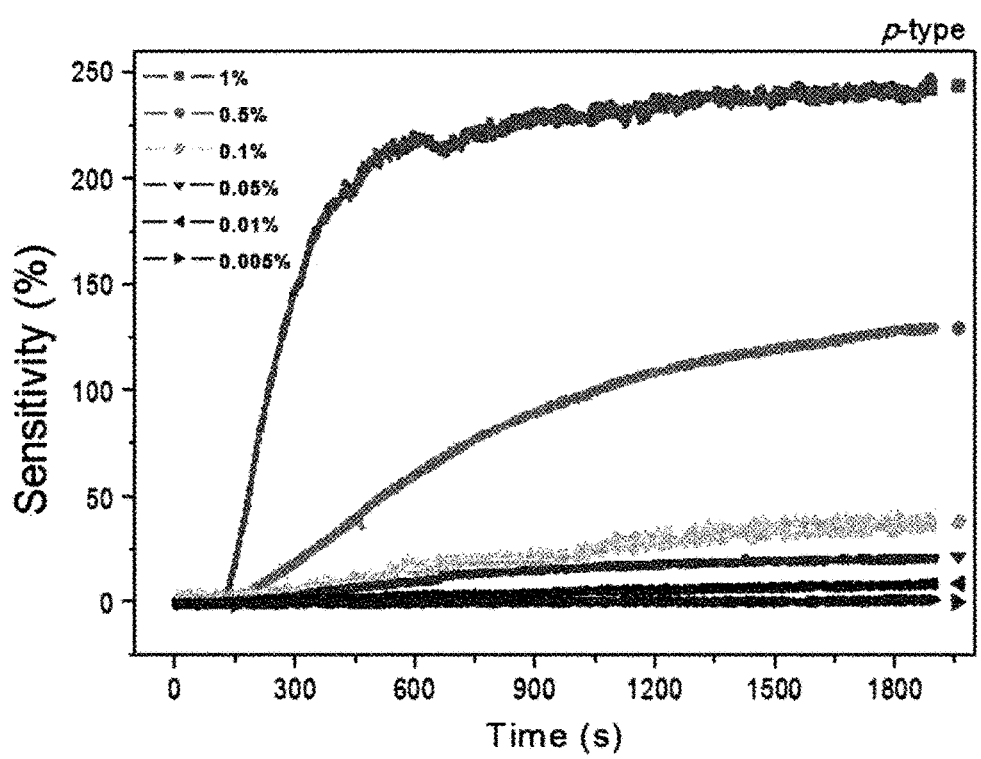
FIG. 7 is a graph illustrating the sensitivity and the reaction time of the hydrogen sensor according to the embodiment of the present invention with respect to the hydrogen exposure in insulating oil based on each hydrogen exposure concentration.
Figure 8:
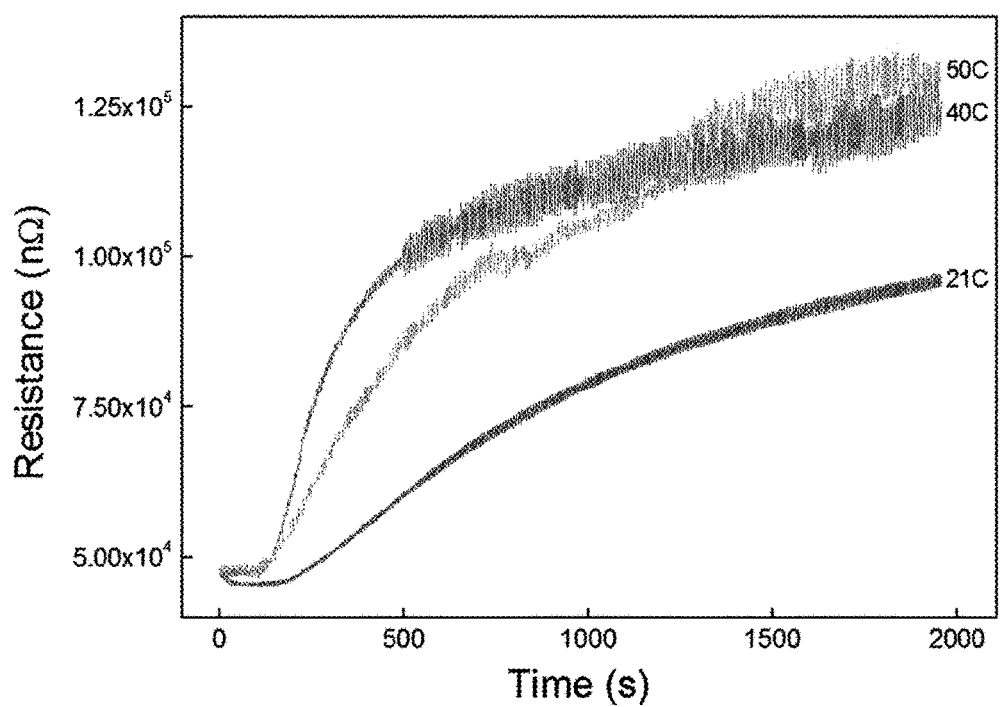
FIG. 8 is a graph illustrating a resistance value and a reaction time of the hydrogen sensor according to the embodiment of the present invention in the insulating oil based on each exposure temperature.

FIG. 7 is a graph illustrating the sensitivity and the reaction time of the P-type silicon nanowire array-based hydrogen sensor according to the embodiment of the present invention with respect to the hydrogen exposure in insulating oil based on each hydrogen exposure concentration. Also, FIG. 8 is a graph illustrating the resistance value and the reaction time of the hydrogen sensor according to the embodiment of the present invention in the insulating oil based on each exposure temperature.

As illustrated in FIG. 7, as the result of monitoring the change in the electrical resistance in real time, it is confirmed that the sensitivity of the hydrogen sensor with respect to hydrogen exposure in insulating oil according to the embodiment of the present invention is 250% and the reaction time ($I_{90}$) thereof is 4 minutes or less. Also, as illustrated in FIG. 8, it is confirmed that the hydrogen sensor according to the embodiment of the present invention maintains similar sensor characteristics even at a high temperature to those at a room temperature.

The preset invention relates to the hydrogen sensor which includes the P-type silicon nanowire array and the hydrogenation catalyst formed on the surface of the nanowire array, and a method of manufacturing the same. The hydrogenation catalyst is reduced into a metal hydride after being exposed to hydrogen, and electrons (e−) may be concentrated at the interface between the nanowire array and the hydrogenation catalyst, and thus the current can be decreased by neutralizing holes inside the nanowire array. Alternatively, the current can be decreased by forming the Schottky contact on the interface between the nanowire array and the hydrogenation catalyst.

Therefore, the hydrogen sensor according to the present invention has a rapid reaction time with respect to hydrogen exposure in oil, water and air and very excellent sensitivity, can be applied to various power facilities such as a transformer in which there is a concern that hydrogen is generated due to the deterioration, and can also be used in human breath analysis.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A hydrogen sensor comprising electrodes and a sensing part positioned between the electrodes, wherein electrical resistance of the sensing part changes with changes in hole concentration, wherein the sensing part comprises:
   a P-type silicon nanowire array comprising a plurality of P-type silicon nanowires; and
   a hydrogenation catalyst formed directly on the entire surface of the P-type silicon nanowires to form a core-shell structure and having a thickness of 1 nm to 20 nm,
   wherein the hydrogenation catalyst is configured to be reduced into a metal hydride (MHx) to form a Schottky contact between the P-type silicon nanowires and the hydrogenation catalyst, and to form a work function of the metal hydride a negative number when exposed to hydrogen such that holes inside the plurality of P-type silicon nanowires are neutralized, and
   wherein a Schottky barrier is formed by a difference between the work function of the metal hydride and the work function of the P-type silicon nanowires, and decreases a current.

2. The hydrogen sensor of claim 1, wherein the nanowire array is doped with a Group III element.

3. The hydrogen sensor of claim 2, wherein a doping amount of the Group III element is $10^{11}$ atoms/cm$^3$ to $10^{20}$ atoms/cm$^3$.

4. The hydrogen sensor of claim 1, wherein a specific resistance value of the nanowire array is 0.001 Ωcm to 10,000 Ωcm.

5. The hydrogen sensor of claim 1, wherein the hydrogenation catalyst includes one or more metals selected from a group consisting of palladium (Pd), platinum (Pt), rhodium (Rd), aluminum (Al), nickel (Ni), manganese (Mn), molybdenum (Mo), magnesium (Mg) and vanadium (V).

6. The hydrogen sensor of claim 1, wherein the hydrogenation catalyst has a thickness of 1 nm to 10 nm.

7. A method for manufacturing a hydrogen sensor, the method comprising:
obtaining a sensing part by:
(a) forming a P-type silicon nanowire array comprising a plurality of P-type silicon nanowires by etching a P-type silicon wafer; and
(b) depositing a hydrogenation catalyst directly on the entire surface of the P-type silicon nanowires to form a core-shell structure having a thickness of 1 nm to 20 nm,
wherein the hydrogenation catalyst is configured to be reduced into a metal hydride (MHx) to form a Schottky contact between the P-type silicon nanowires and the hydrogenation catalyst, and to form a work function of the metal hydride a negative number when exposed to hydrogen such that holes inside the plurality of P-type silicon nanowires are neutralized, and
wherein a Schottky barrier is formed by a difference between the work function of the metal hydride and the work function of P-type silicon nanowires, and decreases a current, and
wherein electrical resistance of the sensing part changes with changes in hole concentration; and
positioning the sensing part between electrodes.

8. The method of claim 7, wherein, in the operation (a), the etching is performed using a silver nitrate ($AgNO_3$) and hydrofluoric acid containing solution which includes 0.25 g to 1 g of silver nitrate per 100 ml of the hydrofluoric acid containing solution.

9. The method of claim 7, wherein, in the operation (a), the etching is performed at 50° C. to 70° C.

10. The method of claim 7, wherein the hydrogenation catalyst has a thickness of 1 nm to 10 nm.

* * * * *